US008235663B2

(12) United States Patent
Rose et al.

(10) Patent No.: US 8,235,663 B2
(45) Date of Patent: Aug. 7, 2012

(54) ARTICLE AND ULTRASONIC INSPECTION METHOD AND SYSTEM THEREFOR

(75) Inventors: Curtis Wayne Rose, Mechanicville, NY (US); Robert Falsetti, Schenectady, NY (US); Gary Lamberton, Glenville, NY (US)

(73) Assignee: General Electric Company, Schenectady, NY (US)

( * ) Notice: Subject to any disclaimer, the term of this patent is extended or adjusted under 35 U.S.C. 154(b) by 792 days.

(21) Appl. No.: 12/332,438

(22) Filed: Dec. 11, 2008

(65) Prior Publication Data

US 2010/0150726 A1 Jun. 17, 2010

(51) Int. Cl.
*F01D 5/00* (2006.01)

(52) U.S. Cl. ...................................... 416/61; 416/220 R

(58) Field of Classification Search .................... 416/61, 416/220 R, 248

See application file for complete search history.

(56) References Cited

U.S. PATENT DOCUMENTS

2005/0207892 A1* 9/2005 Kanebako et al. ........ 416/219 R
2007/0020102 A1* 1/2007 Beeck et al. .............. 416/219 R
2007/0119255 A1* 5/2007 Czerw et al. .................... 73/621

* cited by examiner

*Primary Examiner* — Zandra Smith
*Assistant Examiner* — Jamie C Niesz
(74) *Attorney, Agent, or Firm* — Ernest G. Cusick; Gary M. Hartman; Domenica N. S. Hartman

(57) ABSTRACT

A method, system and article adapted for ultrasonic inspection of the article. The article is disk-shaped and has axially-oriented slots circumferentially spaced from each other at a periphery of the article, with members secured at the periphery of the article such that each member has a retention feature that extends into and engages a corresponding one of the slots so as to secure the members to the slots. Cavities are defined by and between the slots and radially-inward extremities of the retention features within the slots. The inspection method and system entail the use of at least one ultrasonic transducer placed within at least a first of the cavities defined by a first of the slots. The transducer is configured and oriented to perform a diagnostic technique on the article by emitting an ultrasonic signal that intersects an interior surface of a second of the slots immediately adjacent the first slot.

17 Claims, 2 Drawing Sheets

3
14
14
10
12
12
12
18
16
16
16
16
28
30
28
34
34
32
32
32
26
26
24
24
24
24
22
22
3

ARTICLE AND ULTRASONIC INSPECTION METHOD AND SYSTEM THEREFOR

BACKGROUND OF THE INVENTION

The present invention generally relates to articles that benefit from ultrasonic inspection, as well as ultrasonic inspection techniques and systems. More particularly, this invention relates to the ultrasonic inspection of surfaces of axially-oriented slots formed in an article adapted for use in rotating machinery, such as the turbine wheels and rotors of steam and gas turbines.

Ultrasonic inspection techniques have been widely used to perform nondestructive testing on various articles, including those formed of materials with intrinsically coarse grain structures that result in anisotropic and nonuniform acoustic properties. Nonlimiting examples of such articles include forged superalloy turbine wheels (rotors) used in steam and gas turbines. In the hostile operating environments of gas and steam turbines, the structural integrity of a turbine wheel is of great importance in view of the high mechanical stresses that wheels must be able to continuously withstand at extremely high temperatures and rotational speeds.

Ultrasonic inspection techniques employed with turbine wheels have typically involved inspecting the wheel from a plane perpendicular to the highest operating stresses. A typical approach is to place ultrasonic transducers on the fore and/or aft wheel surfaces transverse to the wheel rotational axis. With this approach, ultrasonic energy is generated in a direction substantially perpendicular to the orientation of the most common defects, which tend to lie in axial-radial planes parallel to the fore and aft surfaces of a turbine wheel. Two ultrasonic testing techniques are widely used. The first is a "pitch-catch" technique using two transducers placed on the fore and aft surfaces of the wheel. One of the transducers serves to generate an ultrasonic signal, and ultrasonic signals reflected from acoustical discontinuities are received by the second transducer. The second technique is referred to as "pulse-echo" and makes use of a single transducer to both generate the ultrasonic signal and receive reflected signals.

As well known in the art, the connections that secure turbine buckets (blades) to a turbine wheel are particularly stressed during turbine operation. Such connections are often in the form of complementary retention features defined on the wheel circumference and the roots of the buckets. These retention features, commonly referred to as dovetails, have been used in several different forms. Radial-entry and tangential-entry dovetails are represented in commonly-assigned U.S. Pat. Nos. 6,049,979 and 6,821,086, respectively, and entail one or more male dovetail features that circumferentially extend around the outer periphery of a wheel, and assemble with a complementary female dovetail slot on each bucket. A third dovetail type is the axial-entry dovetail, represented in commonly-assigned U.S. Pat. No. 6,814,543. Axial-entry dovetail connections utilize axially-oriented female slots defined in the wheel circumference, into which a male dovetail of a bucket is inserted in the axial direction of the wheel. Axial-entry dovetails may be straight (typically parallel to the wheel axis) or have a gradual curvature, the latter of which is represented in FIG. 1.

Axial-entry and in particular curved axial-entry dovetail designs are difficult to inspect using conventional ultrasonic pulse-echo techniques due to inadequate detection sensitivity caused by the blade attachment geometry, and particularly the surfaces of the female dovetail slots, which are roughly perpendicular to the fore and aft surfaces of turbine wheel following final machining. As a result, ultrasonic beams projected from these surfaces are not directed perpendicular to defects on the dovetail surfaces. As an alternative, dovetail inspections can be accomplished using pitch-catch techniques by placing transducers opposite each other on the fore and aft faces of a wheel. While capable of providing greater coverage for axial-entry dovetail slots, pitch-catch inspection systems are relatively difficult to set up (for example, transducer placement can be problematic) and are not comparable in sensitivity to pulse-echo inspections. Furthermore, the ultrasonic beams still do not intersect perpendicular to defects located at the interior dovetail surfaces. Regardless of the ultrasonic technique used, the ability to inspect female dovetail surfaces at the circumference of a wheel is exacerbated by the high sonic noise produced by large grain sizes typically found in wheels, as well as a tendency for the acoustic pulse to be steered by flow lines produced during the forging process.

In view of the above, it would be desirable if an improved ultrasonic inspection method were available that was capable of full ultrasonic coverage of surfaces of axial-entry dovetail slots located in the circumference of turbine wheels, as well as interior surfaces of other slots or slot-like features having complex geometries.

BRIEF DESCRIPTION OF THE INVENTION

The present invention provides a method, system and article adapted for ultrasonic inspection of the article, which may be a turbine wheel of a type used in steam and gas turbines, as well as other highly-stressed rotating components having slots in their periphery. Generally, the system and method of this invention are adapted for ultrasonically inspecting a disk-shaped article having a plurality of axially-oriented slots circumferentially spaced from each other at a periphery of the article, with a plurality of members secured at the periphery of the article such that each member has a retention feature that extends into and engages a corresponding one of the slots so as to secure the members to the slots.

According to one aspect of the invention, the method and system make use of at least a first ultrasonic transducer placed within at least a first cavity defined by a first of the slots and radially-inward from a radially-inward extremity of the retention feature within the first slot. The first ultrasonic transducer is configured and oriented to perform a diagnostic technique on the article by emitting an ultrasonic signal that intersects an interior surface of a second slot immediately adjacent the first slot.

According to another aspect of the invention, the inspection method generally includes forming the slots to have radial depths within the article that are greater than the extents to which the retention features of the members extend into the slots, such that the cavities are defined radially-inward from the radially-inward extremities of the retention features. The first ultrasonic transducer is placed in the first cavity defined by the first slot, and the diagnostic technique is performed on the article by causing the first ultrasonic transducer to emit an ultrasonic signal that intersects the interior surface of the second slot immediately adjacent the first slot.

Still another aspect of the invention is the article itself, including the axially-oriented slots circumferentially spaced from each other at a periphery of the article, the members secured at the periphery of the article, and the cavities defined by and between the slots and radially-inward extremities of the retention features within the slots, such that the cavities are radially-inward from the radially-inward extremities of the retention features. The article may be, but is not limited to, a turbine wheel, in which case the slots may be female dovetail slots, the members are buckets, and the retention features of the members may be male dovetails. According to an additional aspect of the invention, the diagnostic technique may be a pulse-echo diagnostic technique, in which case the first ultrasonic transducer receives reflected ultrasonic signals that are returned from the interior surface of the second slot. A second ultrasonic transducer may be placed in a cavity defined by another slot so that the second slot is between the first and second ultrasonic transducers, and the second ultrasonic transducer emits a second ultrasonic signal that intersects a second interior surface of the second slot opposite the interior surface intersected by the ultrasonic signal of the first ultrasonic transducer.

In view of the above, it can be seen that the present invention provides an inspection method and system that can be employed on a turbine wheel, but which entails a modification of conventional turbine wheel geometries to allow insertion of one or more ultrasonic transducers radially inward from the areas of dovetail slots occupied by the buckets (blades) of the wheel. The provision of a cavity in this manner allows the ultrasonic transducer to slide in an axial direction through the wheel in order to ultrasonically interrogate the interior surfaces of the dovetail slots. Positioning of transducers within the dovetail slots enables consistent inspection performance because the transducers remain normal to the critical interior surfaces defined by the lobes (hooks) of the dovetail slots. The method and system can be employed with both straight-through and curved axial-entry wheel dovetail designs.

Additional advantages of the invention include the ability to perform a comprehensive inspection of the dovetail surfaces without requiring bucket removal, thereby simultaneously maximizing inspection capability and minimizing downtime. The invention also offers advantages over pitch-catch ultrasonic inspections, which are more difficult to set up and are not comparable in terms of sensitivity and inspection coverage when attempting to ultrasonically inspect turbine wheels and other articles having complex machined geometries.

Other aspects and advantages of this invention will be better appreciated from the following detailed description.

DETAILED DESCRIPTION OF THE INVENTION

Figure 1:
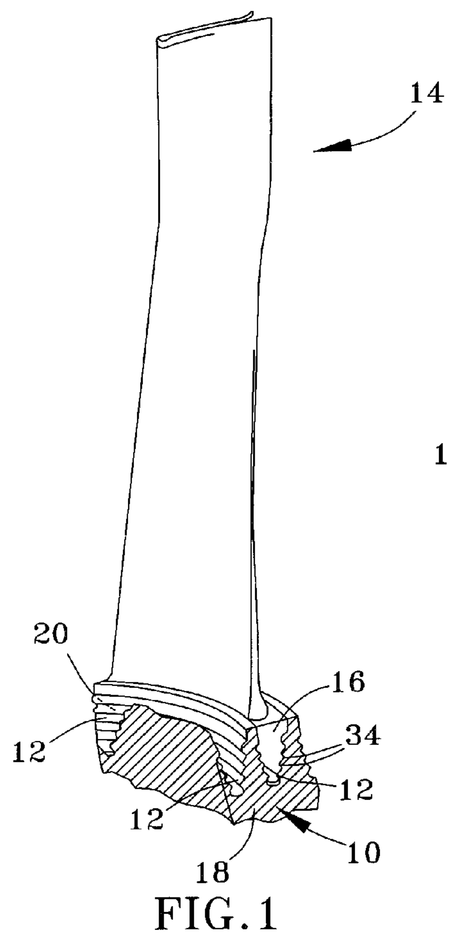
FIG. 1 shows a partial section of a turbine wheel having axial-entry dovetail slots in which buckets are secured in accordance with conventional practice.

FIG. 1 represents a portion of a steam turbine wheel 10 having a curved axial-entry female dovetail slot 12. As well understood in the art, a bucket 14 has been secured to the wheel 10 by axially inserting a male dovetail 16 of the bucket 14 into the dovetail slot 12. The dovetail slot 12 and dovetail 16 are complementary in shape and size to provide a close fit therebetween, such that alternating lobes or hooks 34 of the dovetail slot 12 and dovetail 16 bear against each other when the wheel 10 is rotated at high speeds. Due to their axial-entry configuration, the dovetail slots 12 and the bucket dovetail 16 extend between fore and aft surfaces 18 and 20 of the wheel 10. In addition, the slots 12 are oriented approximately parallel to the rotational axis (not shown) of the wheel 10, about which the wheel 10 is axisymmetric to enable rotation of the wheel 10 at the high rotational speeds required by the turbine in which the wheel 10 is to be used. The wheel 10, bucket 14, and their respective dovetail slot 12 and dovetail 16 are of known configurations in the art, and do not pose any particular limitations to the scope of the invention aside from their representation of an axial-entry dovetail design.

Figure 3:
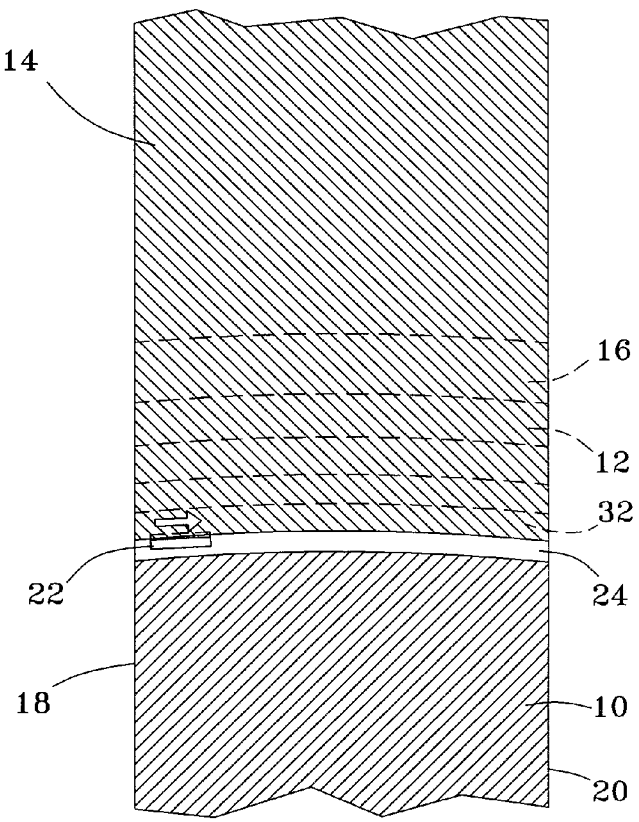
FIG. 3 is a partial cross-sectional view of the wheel of FIG. 2 along line 3-3.
Figure 2:
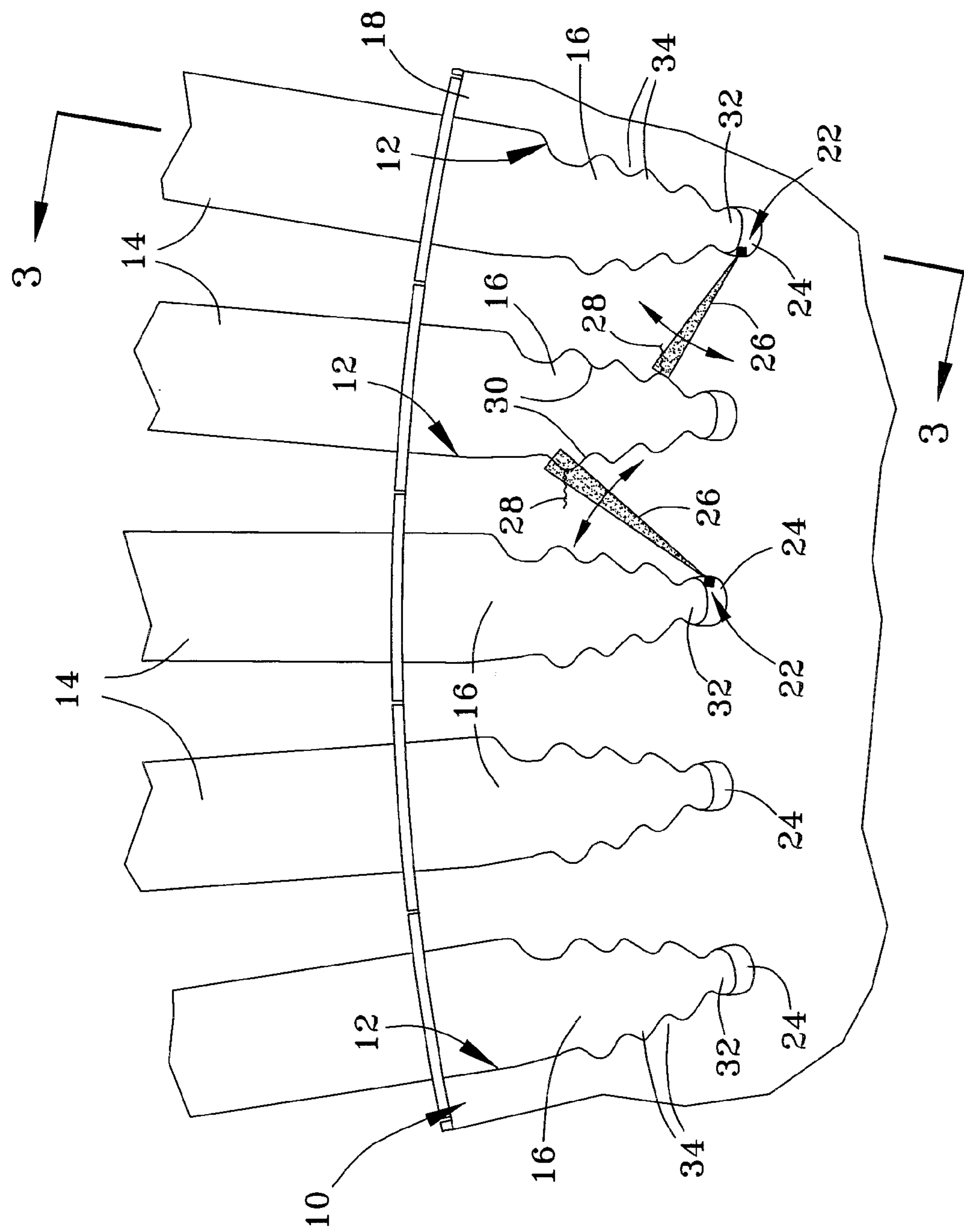
FIG. 2 is a view taken from a fore or aft surface of a wheel, such as the wheel of FIG. 1, and shows five buckets assembled with the wheel and ultrasonic transducers placed in two of the dovetail slots for inspection of a third dovetail slot therebetween.

From FIG. 1, the complex geometries of the interior surfaces of the dovetail slots 12 are evident, making any ultrasonic inspection for defects located at these surfaces very difficult using conventional methods. As represented in FIGS. 2 and 3, a particular aspect of the present invention is to allow for ultrasonic inspection of the dovetail surfaces 30 of a given slot 12 with an ultrasonic transducer unit 22 placed in a slot 12 located circumferentially to either side of the inspected slot 12. While two transducer units 22 are shown in FIG. 2, it should be understood that a single transducer unit 22 can be placed in one slot 12 to inspect one surface 30 of the inspected slot 12, and then moved and placed in the slot 12 on the opposite side of the inspected slot 12. The transducer units 22 are received in cavities 24 present at the radially inward extent of each bucket dovetail 16 as a result of the wheel dovetail slots 12 being machined or otherwise formed to extend farther in the radial direction of the wheel 10 than is required to accommodate the bucket dovetails 16. Aside from the cavities 24, each dovetail slot 12 and its respective bucket dovetail 16 are complementary in size and shape to provide a close fit between the two in order to secure the buckets 14 under the very high dynamic loads imposed during turbine operation.

The cross-sectional shape of each cavity 24 is represented as a continuous curved contour to minimize stress concentrations, though it is foreseeable that other cavity shapes could be employed. The cross-sectional size of each cavity 24 must be sufficiently large to accommodate at least one transducer unit 22 and to permit free travel of the transducer unit 22 in the axial direction of the wheel 10 (represented by the arrow in FIG. 3). Otherwise, the cross-sectional size of each cavity 24 is preferably no larger than necessary to accommodate the transducer unit 22 in order to maximize the structural integrity of the wheel 10. In FIGS. 2 and 3, the cross-sectional area of each cavity 24 is represented as roughly equal to about one-half of the nearest (and smallest) lobe 32 of the bucket dovetail 16, though larger and smaller cross-sections are foreseeable.

As depicted in FIGS. 2 and 3, the transducer units 22 are less than half the cross-sectional size of the cavities 24, and each unit 22 is positioned entirely within the side of its respective cavity 24 closest to the dovetail slot 12 being inspected. Furthermore, each unit 22 generates one or more ultrasonic beams 26 that can be projected onto defects 28 (e.g., cracks) present at the interior surfaces 30 of the inspected slot 12. The units 22 are preferably configured to enable their one or more beams 26 to interrogate the entire radial length of the nearest surface 30 of the inspected slot 12. The transducer units 22 are also preferably capable of being moved axially through their respective cavities 24 so that the surfaces 30 can be inspected in their entirety between the fore and aft surfaces 18 and 20 of the wheel 10. Numerous configurations for the transducer units 22 are within the scope of this invention. For example, each transducer unit 22 may comprise a housing having a surface shaped to closely match the shape of the surface of the cavity 24 it abuts. The housings of the transducer units 22 can be formed of the same or similar material as the wheel 10, so that the sound velocity in the unit housing is the same or nearly the same as in the wheel 10, so that the effect of the curvature of the cavity 24 is minimal. A suitable couplant, such as a lightweight oil, can be applied between each transducer unit 22 and the mating surface of its cavity 24 to further reduce the effect of the interface between the transducer units 22 and their cavities 24.

The preferred inspection technique for use with the invention is the pulse-echo technique in which a single transducer is adapted to generate an ultrasonic beam and receive the reflected signal. The pulse-echo technique is preferred in the present invention because it is capable of receiving the reflected signals without degradation of test sensitivity over the distances of interest, whereas ultrasonic inspections performed with the pitch-catch ultrasonic technique would likely miss areas that require inspection. Suitable transducers for the transducer units 22 include a variety of types capable of use in ultrasonic inspection procedures, such as monolithic ultrasonic angle beam transducers and phased array type transducers. Nonlimiting examples include ultrasonic transducers commercially available from Krautkramer, Inc., as well as other manufacturers.

Multiple transducers can be arranged as a linear array within each transducer unit 22 and share a single pulser. The transducers produce a longitudinal wave at a fixed angle, and groups of transducers can be pulsed simultaneously or multiplexed to simulate movement of the beam 26 along the radial length of the dovetail slot 12 being inspected, as indicated by the arrows indicating a scanning effect achieved with the beams 26 in FIG. 2. Alternatively, the transducer units 22 can be rotated to provide radial coverage along the radial length of the inspected slot 12.

As the term "phased array" is conventionally understood in the art, the transducer unit 22 would comprise a series of individual ultrasonic transducers arranged in a row and acoustically isolated from each other. Contrary to a linear array transducer unit, each phased array transducer has its own electrical connection and pulser, and each produces its own time/amplitude response ("A-scan"), which can then be summed and graphically displayed. The angle of the ultrasonic beam 26 generated by each transducer can be varied (steered) as well as the mode and focus of the beam 26 by controlling the timing of the pulse and reception for each individual transducer. The advantage of using a phased array transducer unit 22 in the inspection method of this invention is the ability to focus the ultrasonic beam 26 at a specific target 28 at a specific depth. This focusing of the beam 26 counteracts the negative effect that the curvatures of the cavities 24 and dovetail surfaces 30 have on the sound field, which would tend to disperse the beam 26 and reduce the sound amplitude reflected from a defect 28.

According to an aspect of the invention, the location of the transducer unit 22 within a slot 12 allows the ultrasonic beam 26 to travel roughly perpendicular to the adjacent axially-extending surface 30 of the dovetail slot 12, so that the beam 26 intersects defects 28 throughout the volume of the wheel 10 between the cavity 24 and the slot surface 30, as shown in FIG. 3. In addition to the scanning effect discussed above, during inspection the transducer unit 22 can be caused to travel in the axial direction of the wheel 10 (FIG. 3) between the fore and aft wheel surfaces 18 and 20. The length of the unit 22 is preferably selected so that the unit 22 is able to navigate curved axial-entry dovetail designs such as that represented in FIG. 1. The volume of material that can be inspected positively coincides with the region within the wheel 10 in which defects 28 capable of shortening the life of the wheel 10 can occur. Each dovetail slot 12 of the wheel 10 is inspected by a transducer unit 22 located in an immediately adjacent slot 12, which in typical wheel and dovetail configurations will place the transducer unit 22 about two to about six inches (about five to fifteen centimeters) or more from the dovetail surface 30 being inspected. A single transducer unit 22 can be positioned on the side of a cavity 24 to inspect the nearest adjacent dovetail slot 12, and then shifted to the other side of the cavity to inspect the slot 12 nearest the other side of the cavity 24. All slots 12 of the wheel 10 can be inspected by sequentially moving a single transducer unit 22 around the circumference of the wheel 10. In this manner, the invention is capable of allowing full ultrasonic test coverage of the wheel dovetail slot surfaces 30 using the pulse-echo technique without degradation of test sensitivity over the full test distance between the cavities 24 and the radially outermost extents of the dovetail slot surfaces 30. As evident from FIGS. 2 and 3, inspection of the dovetail slots 12 of the wheel 10 can be performed as part of an in-service inspection without requiring removal of the buckets 14.

While the invention has been described in terms of particular embodiments, it is apparent that other forms could be adopted by one skilled in the art. For example, the physical configurations of the transducer units 22 and the article (e.g., wheel 10) being inspected, including its buckets 14, dovetail slots 12, and bucket dovetails 16, could differ from that shown. Therefore, the scope of the invention is to be limited only by the following claims.

The invention claimed is:

1. A method of ultrasonically inspecting a disk-shaped article having a plurality of axially-oriented slots circumferentially spaced from each other at a periphery of the article and circumferentially separated from each other by volume portions of the article, the article comprising a plurality of members secured at the periphery of the article, each member having a retention feature that extends into and engages a corresponding one of the slots so as to secure the members to the slots, the method comprising the steps of:

forming the slots to have radial depths within the article that are greater than an extent to which the retention features of the members extend into the slots so as to define cavities radially-inward from radially-inward extremities of the retention features, the cavities accommodating at least a first ultrasonic transducer adapted to be placed in the slots without requiring removal of the members;

placing at least the first ultrasonic transducer in at least a first of the cavities defined by a first of the slots; and performing a diagnostic technique on an interior surface of a second of the slots that is immediately adjacent the first slot by causing the first ultrasonic transducer to emit an ultrasonic signal that passes through one of the volume portions of the article between the first cavity and the interior surface of the second slot so that the ultrasonic signal intersects the interior surface of the second slot.

2. The method according to claim 1, wherein the diagnostic technique is a pulse-echo ultrasonic diagnostic technique, and the first ultrasonic transducer receives a reflected ultrasonic signal that is returned from the interior surface.

3. The method according to claim 1, wherein the first ultrasonic transducer is one of an array of ultrasonic transducers placed in the first cavity, the ultrasonic transducers being pulsed simultaneously during the performing step to generate a plurality of ultrasonic signals.

4. The method according to claim 1, wherein the first ultrasonic transducer is one of an array of ultrasonic transducers placed in the first cavity, at least some of the ultrasonic transducers being pulsed at different times during the performing step to generate a plurality of ultrasonic signals.

5. The method according to claim 1, wherein the first ultrasonic transducer is one of a phased array of ultrasonic transducers placed in the first cavity, the phased array of ultrasonic transducers being operated to generate and focus a plurality of ultrasonic signals at predetermined depths from the first cavity.

6. The method according to claim 1, wherein the article has an axis of rotation, an axisymmetric configuration, and oppositely-disposed fore and aft surfaces, and the first cavity is continuous between the fore and aft surfaces.

7. The method according to claim 6, wherein the first cavity is approximately parallel but curved relative to the axis of rotation of the article.

8. The method according to claim 1, wherein the first ultrasonic transducer is sized and configured to be positioned entirely within one half of the first cavity nearest the second slot.

9. The method according to claim 1, wherein the article is a turbine wheel, the slots are female axial-entry dovetail slots, the members are buckets, and the retention features of the members are male dovetails.

10. An ultrasonic inspection system for a disk-shaped article having a plurality of axially-oriented slots circumferentially spaced from each other at a periphery of the article and circumferentially separated from each other by volume portions of the article, the article comprising a plurality of members secured at the periphery of the article, each member having a retention feature that extends into and engages a corresponding one of the slots so as to secure the members to the slots, the ultrasonic inspection system comprising:

at least a first ultrasonic transducer within at least a first cavity defined by a first of the slots and radially-inward from a radially-inward extremity of the retention feature of a first of the members within the first slot, the first cavity accommodating the first ultrasonic transducer without requiring removal of the first member from the first slot, the first ultrasonic transducer being configured and oriented to perform a diagnostic technique on an interior surface of a second of the slots that is immediately adjacent the first slot by emitting an ultrasonic signal that passes through one of the volume portions of the article between the first cavity and the interior surface of the second slot so that the ultrasonic signal intersects the interior surface of the second slot.

11. The ultrasonic inspection system according to claim 10, wherein the diagnostic technique is a pulse-echo ultrasonic diagnostic technique and the first ultrasonic transducer is configured to receive a reflected ultrasonic signal returned from the interior surface.

12. The ultrasonic inspection system according to claim 10, wherein the first ultrasonic transducer is one of an array of ultrasonic transducers placed in the first cavity and adapted to generate a plurality of ultrasonic signals.

13. The ultrasonic inspection system according to claim 10, wherein the first ultrasonic transducer is one of a phased array of ultrasonic transducers placed in the first cavity and adapted to generate and focus a plurality of ultrasonic signals at predetermined depths from the first cavity.

14. The ultrasonic inspection system according to claim 10, wherein the article has an axis of rotation, an axisymmetric configuration, and oppositely-disposed fore and aft surfaces, and the first cavity is continuous between the fore and aft surfaces.

15. The ultrasonic inspection system according to claim 14, wherein the first cavity is approximately parallel but curved relative to the axis of rotation of the article.

16. The ultrasonic inspection system according to claim 10, wherein the first ultrasonic transducer is positioned entirely within one half of the first cavity nearest the second slot.

17. The ultrasonic inspection system according to claim 10, wherein the article is a turbine wheel, the slots are female axial-entry dovetail slots, the members are buckets, and the retention features of the members are male dovetails.

* * * * *